United States Patent [19]

Kamei et al.

[11] Patent Number: 5,130,460

[45] Date of Patent: Jul. 14, 1992

[54] SILOXANE COMPOUND CONTAINING HYDROXYPHENYL GROUP

[75] Inventors: Masanao Kamei; Shoji Ichinohe, both of Gunma, Japan

[73] Assignee: Shin-Etsu Chemical Co., Ltd., Tokyo, Japan

[21] Appl. No.: 485,707

[22] Filed: Feb. 27, 1990

[30] Foreign Application Priority Data

Feb. 27, 1989 [JP] Japan ................................. 1-48069

[51] Int. Cl.$^5$ ............................ C07F 7/08; C07F 7/18
[52] U.S. Cl. ............................................. 556/449
[58] Field of Search .......................... 556/449

[56] References Cited

U.S. PATENT DOCUMENTS

| | | | |
|---|---|---|---|
| 3,328,450 | 6/1967 | Plueddemann | 556/449 X |
| 3,579,467 | 5/1971 | Brown | 556/449 X |
| 3,586,705 | 6/1971 | Owen et al. | 556/449 X |
| 4,132,702 | 1/1979 | Schmidt et al. | 556/449 X |

FOREIGN PATENT DOCUMENTS

| | | |
|---|---|---|
| 2364841 | 7/1974 | Fed. Rep. of Germany ...... 556/449 |
| 2364887 | 7/1974 | Fed. Rep. of Germany ...... 556/449 |

Primary Examiner—Paul F. Shaver
Attorney, Agent, or Firm—Millen, White & Zelano

[57] ABSTRACT

A hydroxyphenyl group-containing siloxane compound represented by the following general formula (I), containing at least one $R^2$ in a molecule to acquire an aptitude for modification of polycarbonate and polyester resins:

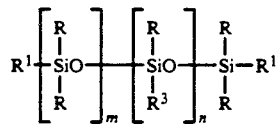

wherein R represents an alkyl group containing 1 to 4 carbon atoms; $R^3$ represents a monovalent organic group containing 1 to 20 carbon atoms; $R^1$ represents R or $R^2$; $R^2$ represents

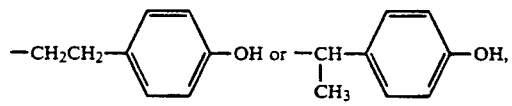

m and n are each 0 or a positive integer, provided that m+n is 1 or above, and at least one $R^1$ is $R^2$ when n is 0.

8 Claims, 3 Drawing Sheets

SILOXANE COMPOUND CONTAINING HYDROXYPHENYL GROUP

FIELD OF THE INVENTION

This invention relates to a novel siloxane compound containing hydroxyphenyl group and, more particularly, tok a hydroxyphenyl group-containing siloxane compound suitable for the modification of polycarbonate or polyester.

BACKGROUND OF THE INVENTION

Hitherto, polyester and polycarbonate resins have been modified with hydroxyphenyl group-containing silicone compounds for the purpose of improving physical characteristics such as flexibility, heat resistance, low temperature characteristics, etc., and surface characteristics such as slippability, water repellency, etc.

For instance, siloxane compounds represented by the general formula (II) are disclosed in U.S. Pat. Nos. 3,182,662 and 3,419,634 as the compounds for producing silicone-modified polycarbonate resins:

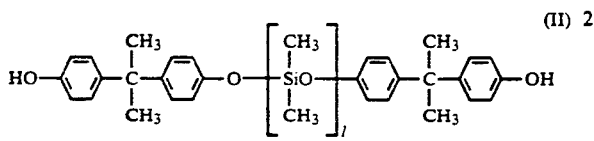
(II)

While the foregoing siloxane compounds can readily undergo a modification reaction because their hydroxyl groups are located at the para-position of phenyl group, the polycarbonate resins produced, which have the following general formula (III), have a defect in that the stability to hydrolysis is low because of the introduction of Si-O-C linkage into the polymer chain:

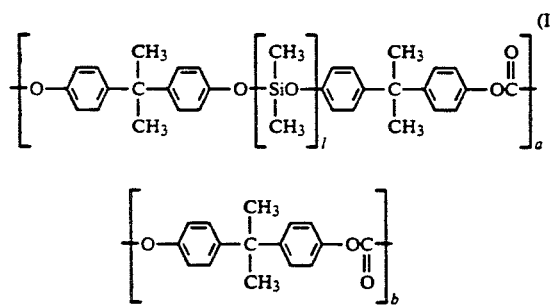
(III)

Even if one thus wanted to produce such a hydroxyphenyl group-containing silicone as represented by the following formula,

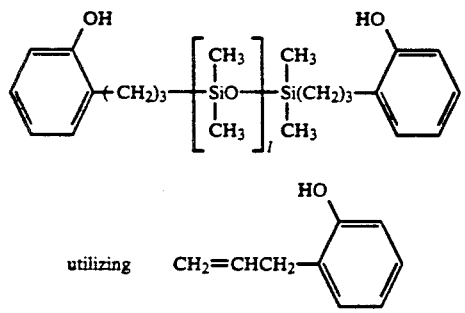

utilizing $CH_2=CHCH_2-$ so that the Si-O-C linkage would not be contained, therein the corresponding silicone-modified polycarbonate resins cannot be obtained because the reactivity between the foregoing phenol compound and phosgene is low due to the presence of OH group at the ortho-position of phenyl group in the phenol compound.

As a result of concentrating our energies on obviating the above-described defects, it has now been found that a slioxane compound containing in a molecule at least one hydroxyphenyl group of the formula,

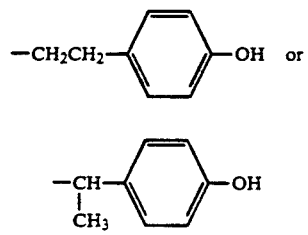

is very useful in the production of silicone-modified polyester and polycarbonate resins, thus achieving this invention.

SUMMARY OF THE INVENTION

Therefore, a first object of this invention is to provide a hydroxyphenyl group-containing siloxane compound which has high rectivity and is best fitted for modification into polyester and polycarbonate resins.

A second object of this invention is to provide a hydroxyphenyl group-containing siloxane compound which is highly stable to hydrolysis, and well suited to produce silicone-modified polyesters and silicone-modified polycarbonates.

The above-described objects are attained with a hydroxyphenyl group-containing compound represented by the following general formula (I), which is characterized by the presence of at least one $R^2$ in a molecule:

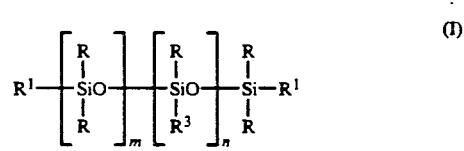
(I)

wherein R represents an alkyl group containing 1 to 4 carbon atoms; $R^3$ represents a monovalent organic group containing 1 to 20 carbon atoms; $R^1$ represents R or $R^2$; $R^2$ represents

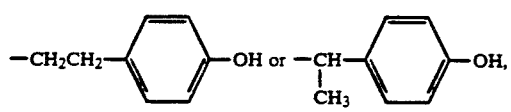

m and n ore each 0 or a positive integer, provided that m +n is 1 or above, and at least one $R^1$ is $R^2$ when n is 0.

Not only do the hydroxyphenyl group-containing siloxane compounds of this invention have high reactivity and are well suited for modification of polycarbonate resins and polyester resins, but alos th% resins modified with a siloxane compound of this invention acquire extreme usefulness because of their excellent in surface characteristics such as slippability, water repelling property, etc., as well as in physical characteristics such as flexibility, low temperature characteristics, etc.

DETAILED DESCRIPTION OF THE INVENTION

Figure 1:
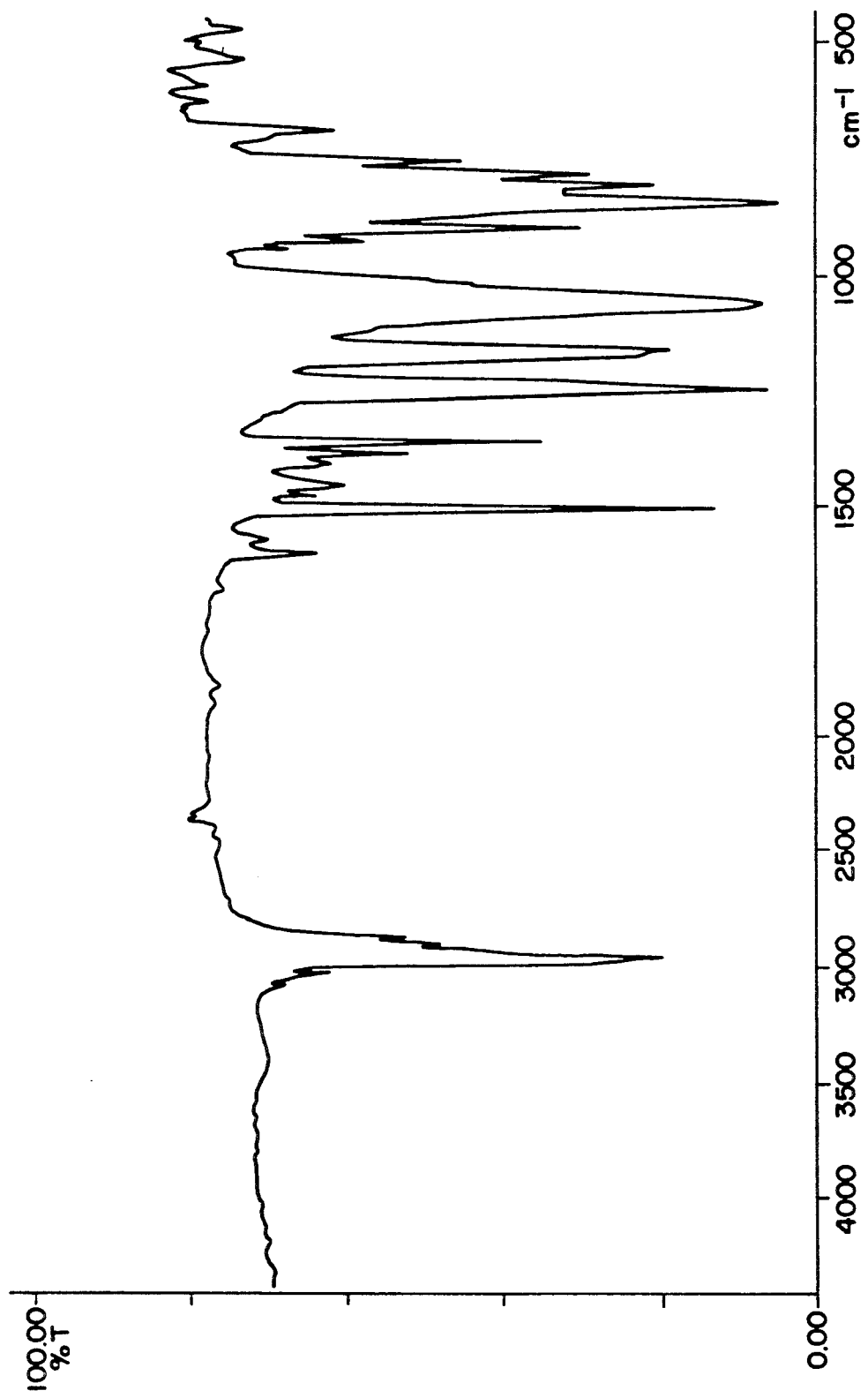
FIG. 1 is an infrared absorption spectrum of the mixture of the compounds (VII) and (VII) obtained in Example 1.

The hydrowyphenyl group-containing siloxane compounds of this invention, which can be represented by the general formula (I),

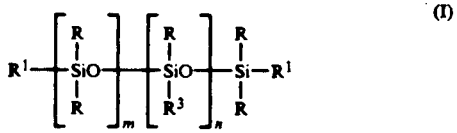

can be obtained using p-tert-butoxystyrene of the formula (V) as a starting material:

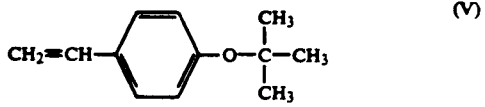

More specifically, a Si-H moiety-containing siloxane and the above-illustrated p-tert-butoxystyrene are submitted to addition reaction in the presence of chloroplatinic acid as a catalyst to produce the corresponding adduct of the general formula (VI):

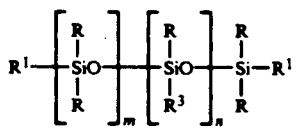

wherein R represents an alkyl group containing 1 to 4 carbon atoms; $R^3$ represents a monovalent organic group containing 1 to 20 carbon atoms; $R^1$ represents R,

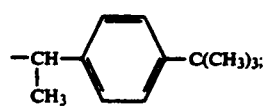

m and n are each 0 or a positive integer, provided that m + n is 1 or above, and at least one $R^4$ not R.

In the above-described addition reaction, isomerization occurs to produce a mixture of both a compound containing as on $R^4$ group the group of

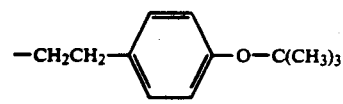

and a compound containing as and $R^4$ group the group of

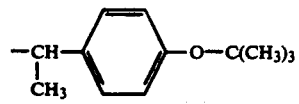

The reaction is effected under a reaction temperature of from 0° to 150° C., preferably from 50° to 120° C., using no solvent or such a solvent as not to have any active hydrogen, e.g., an aromatic hydrocarbon such as toluene, xylene, etc., an aliphatic hydrocarbon such as hexane, octane, etc., an ester such as ethyl acetate, butyl acetate, etc., or a chlorinated hydrocarbon such as carbon tetrachloride, trichloroethane, etc. As examples of catalysts suitable for the addition reaction, mention may be made of known ones such as platinum, palladium and rhodium complexes.

Then, an organic solvent, methanol and concentrated hydrochloric acid are added to the above-described addition product (VI), and stirred for 24 hours at room temperature to yield the desired hydroxyphenyl group-containing siloxane compound (I). Examples of the organic solvent usable in the foregoing reaction include ethers such as tetrahydrofuran, diethylether, dibutylether, etc., and aromatic hydrocarbons such as toluene, xylene, etc. An amount of concentrated hydrochloric acid used therein ranges from 0.5 to 3.0 g, preferably from 1.0 to 2.0 g, per 10 mmol of hydroxyphenyl group. The thus obtained hydroxyphenyl group-containing siloxane compound is made to react with phosgene or carboxylic acid to easily produce a silicone-modified polycarbonate or polyester resin which has excellent stability to hydrolysis.

EXAMPLE

This invention will now be illustrated in more detail by reference to the following examples. However, the invention should not be construed as being limited to these examples.

EXAMPLE 1

In a 300 ml flask equipped with a stirrer and a condenser, 89 g (0.6 mol) of pentadimethyldisiloxane was placed, and thereto was added 0.05 g of a 2% isopropyl alcohol solution of chloroplatinic acid. The resulting mixture was heated with an oil bath so that the inside temperature was kept at 70° C. and thereto, 88 g (0.5 mol) of p-tert-butoxystyrene (V) was added dropwisely with stirring. After the conclusion of the dropwise addition, the reaction mixture was further stirred for 1 hour at 80° C., and then it was checked by gas chromatography whether p-tert-butoxystyrene (V) added as a starting material remained or not. Therein, the disappearance of p-tert-butoxystyrene was ascertained.

The reaction product was distilled to yield 137 g of the mixture of the compound,

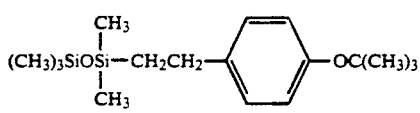

(VII)

and the compound

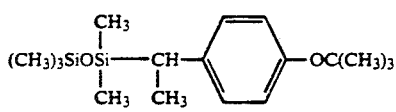

(VIII)

This mixture had a boiling point of 132°–134° C/4 mmHg, and a yield thereof was 85%.

The above-illustrated mixture was identified using $^1$H-NMR and GC-MS (Gas Chromatography-Mass Spectormetry) analyses. In addition, it had an infrared absorption spectrum shown in FIG. 1.

$^1$H-NMR: δ (ppm);
Internal Standard: $CH_2C\delta_2$,
Solvent: $CDC\delta_3$.

Compound (VII):

0.2(Si—$CH_3$, S, 6H)
  0.3(Si—$CH_3$, S, 9H)
  0.9(Si—$CH_2$—, m, 2H)
  1.3(C—$CH_3$, S, 9H)
  2.7(—$C_6H_4$—$CH_2$, m, 2H)
  6.9(—$C_6H_4$—, m, 4H)

Compound (VIII):

0.2(Si—$CH_3$, S, 6H)
  0.3(Si—$CH_3$, S, 9H)
  1.3(—C—$CH_3$, S, 9H)
  1.4(Si—C—, S, 3H)
       |
       $CH_3$
  2.1(Si—CH—, m, 1H)
  7.0(—$C_6H_4$—, m, 4H)

As the result of GC-MS analysis, the value of m/e was found to be 324 in both the compounds (VII) and (VIII).

A 9.7 g (30 mmol) portion of the above-described mixture of the compounds (VII) and (VIII), 25 g of tetrahydrofuran, 15 g of methanol and 4.5 g of concentrated hydrochloric acid were mixed, and submitted to a reaction for 24 hours. Thereafter, the completion of the reaction was checked by gas chromatography, and the result thereof supported the disappearance of the compounds (VII) and (VIII) used as a starting material.

After the conclusion of the reaction, the waste acid was separated by teh addition of 15 g of toluene and 20 g of water, and distillation was carried out after washing.

Thus, 7 g of the mixture of

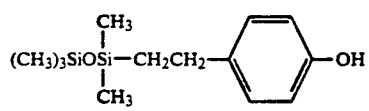

(IX)

and

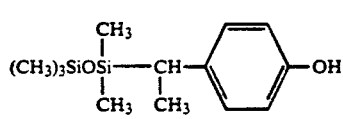

(X)

was obtained. The yield thereof was 88%.

Figure 2:
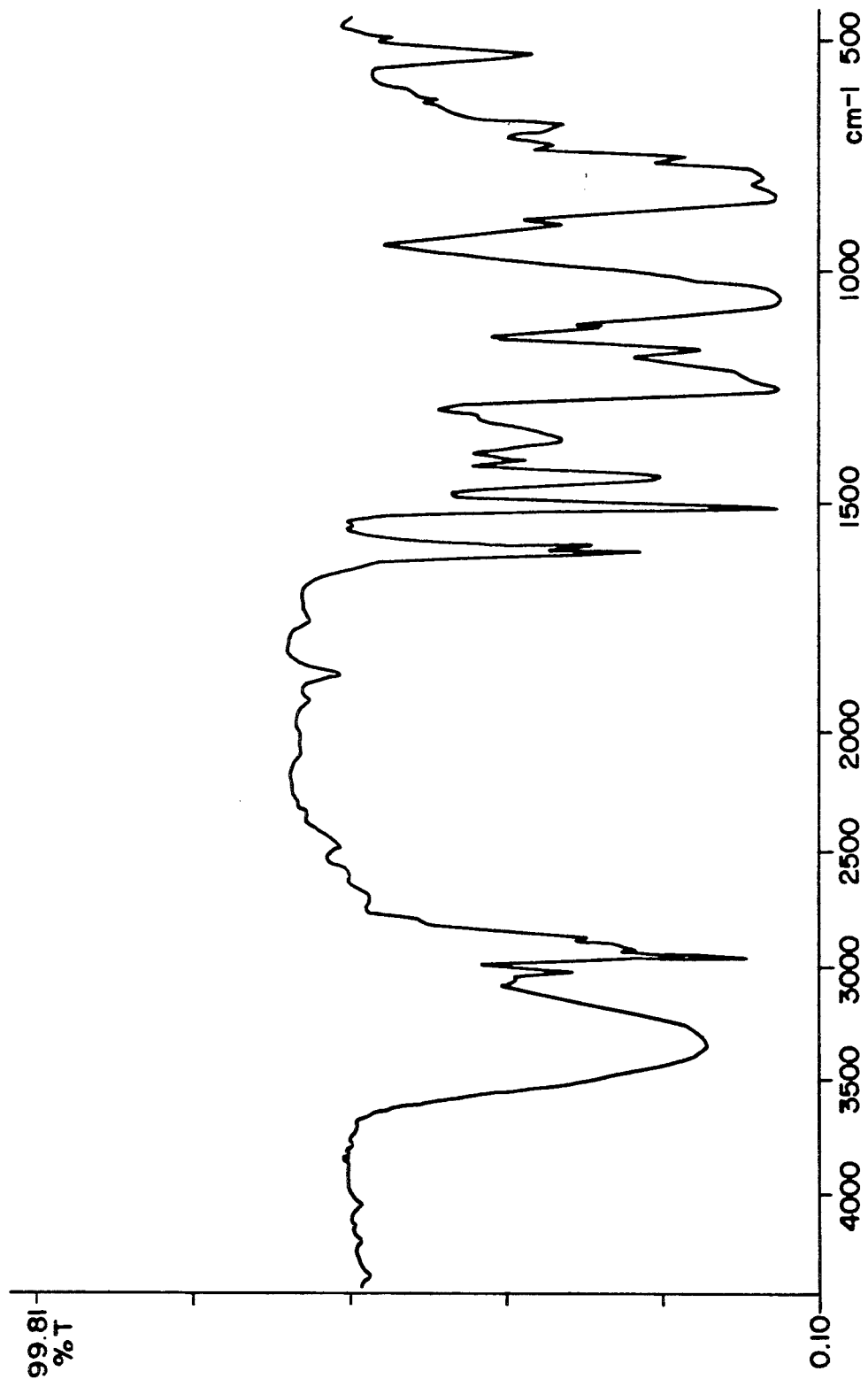
FIG. 2 is an infrared absorption spectrum of the mixture of the compounds (IX) and (X) obtained in Example 1.
Figure 3:
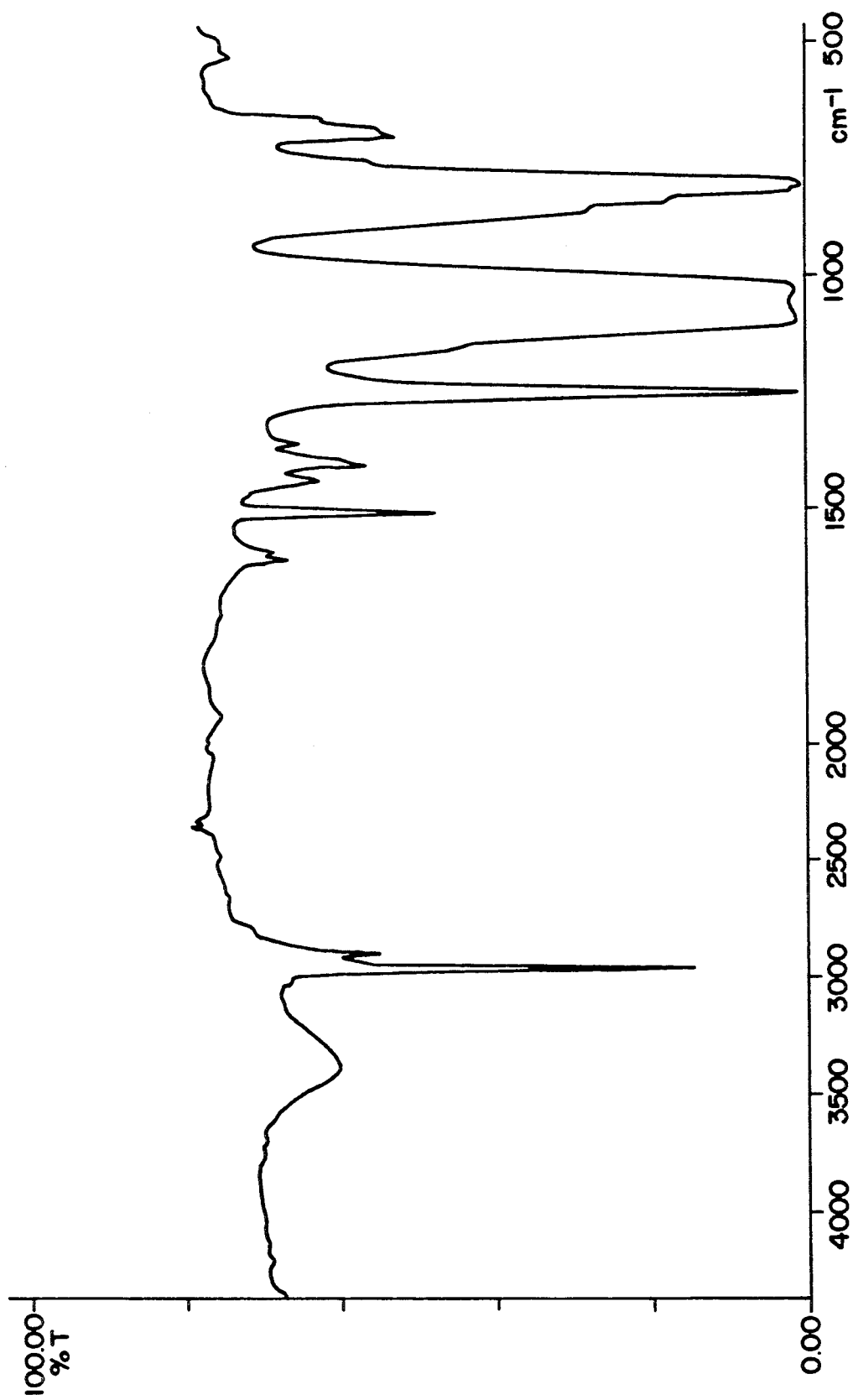
FIG. 3 is an infrared absorption spectrum of the mixture of the compounds (XI) and (XII) obtained in Example 2.

The above-illustrated compounds (IX) and (X) were identified by $^1$H-NMR analysis and GC-MS analysis. In addition, an infrared absorption spectrum shown by the mixture of such compounds was given in FIG. 2.

$^1$H-NMR: δ (ppm);
Internal Standard: $CH_2C\delta_2$, Sovent: $CDC\delta_3$.

Compound (IX):

0.2(Si—$CH_3$, S, 6H)
  0.3(Si—$CH_3$, S, 9H)
  0.9(Si—$CH_2$—, m, 2H)
  2.7(—$C_6H_4$—$CH_2$, m, 2H)
  6.1(—OH, S, 1H)
  7.0(—$C_6H_4$—, m, 4H)

Compound (X):

0.2(Si—$CH_3$, S, 6H)
  0.3(Si—$CH_3$, S, 9H)
  1.4(Si—C—, S, 3H)
       |
       $CH_3$
  2.1(Si—CH—, m, 1H)
  6.2(—OH, S, 1H)
  7.1(—$C_6H_4$—, m, 4H)

As the result of GC-MS analysis, the value of m/e was found to be 268 in both the compounds (IX) and (X).

EXAMPLE 2

In a one-litre flask equipped with a stirrer and a condenser, 370 g (0.25 mol) of one-end-hydrogen siloxane of the formula,

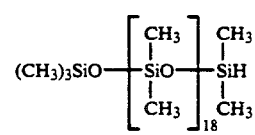

was placed, and thereto was added 01. g of a 2% isopropyl alcohol solution of chloroplatinic acid. The resulting mixture was heated with an oil bath so that the inside temperature was kept at 70° C. and thereto, 50 g (0.28 mol) of p-tert-butoxystyrene (V) was added dropwisely with stirring. The reaction was run at 80° C. for 2 hours. After the disappearance of substantially all the Si-H bond was ascertained, the reaction product was cooled, admixed with 300 g of tetrahydrofuran, 150 g of methanol and 30 g of concnetrated hydrochloric acid, and submitted to a reaction for 36 hours at room temperature. After the conclusion of the reaction, the waste acid was separated by the addition of toluene and water, and the solvent was distilled away after washing. Thus, 370 g of the mixture of hydroxyphenyl group-containing siloxanes (XI) and (XII) having the following structural formulae, respectively, was obtained. The yield thereof was 92%.

(XI)

$(CH_3)_3SiO \left[ \begin{array}{c} CH_3 \\ | \\ SiO \\ | \\ CH_3 \end{array} \right]_{18} \begin{array}{c} CH_3 \\ | \\ Si-CH_2-CH_2- \\ | \\ CH_3 \end{array} \text{—}\!\!\bigcirc\!\!\text{—} OH$ -continued

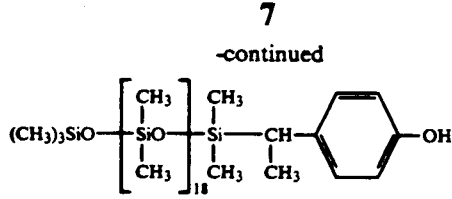
(XII)

According to the molecular weight measurement by GPC (gel permeation chromathography), the mixture had a number average molecular weight (Mn) of 1,900 based on polystyrene, and a weight average molecular weight (Mw) of 2,300 based on polystyrene. The degree of polydispersibility (Mn/Mw) was 1.2, and the hydroxy value was 37 (KOH mg/g), which was in good agreement with the theoretical value 34.

EXAMPLE 3

In a one-litre flask equipped with a stirrer and a condenser, 366 g (0.25 mol) of both-end-hydrogen siloxane having the following formula on an average,

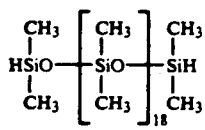

was placed, and thereto was added 0.1 g of a 2% isopropyl alcohol solution of chloroplatinic acid. The resulting mixture was heated with an oil bath so that the inside temperature was kept at 70° C. and thereto, 93 g (0.53 mol) of p-tert-butoxystyrene (V) was added dropwisely with stirring. The reaction was run at 80° C. for 2 hours. After the disappearance of substantially all the Si-H bonds was ascertained, the reaction product was cooled, admixed with 300 g of tetrahydrofuran, 150 g of methanol and 50 g of concentrated hydrochloric acid, and submitted to a reaction for 36 hours at room temperature. After the conclusion of the reaction, the waste acid was separated by the addition of toluene and water, and the solvent was distilled away after washing. Thus, 400 g of the mixture of hydroxyphenyl group-continuing siloxanes (XIII), (XIV) and (XV) having the following structural formulae, respectively, was obtained in a 88% yield.

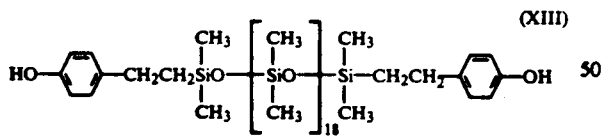
(XIII)

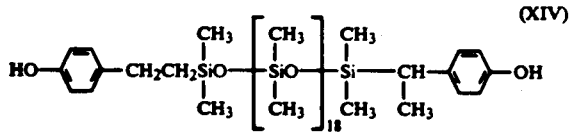
(XIV)

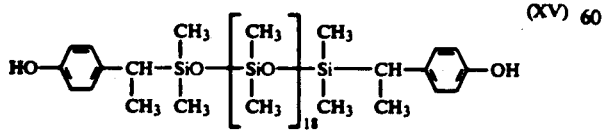
(XV)

According to the molecular weight measurement by GPC, the mixture had a number average molecular weight (Mn) of 2,000 based on polystyrene, and a weight average molecular weight (Mw) of 4,2000 based on polystyrene. The degree of polydispersibility (Mn/Mw) was 2.1, and the hydroxyl value was 65 (KOH mg/g), which was in good agreement with the theoretical value 62.

What is claimed is:

1. A process for the preparation of at least one hydroxyphenyl group-containing siloxane compound represented by the following general formula (I)

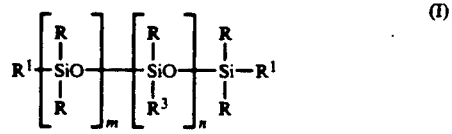
(I)

wherein R represents an alkyl group of 1 to 4 carbon atoms, $R^3$ represents a monovalent organic group of 1 to 20 carbon atoms; $R^1$ represents R or $R^2$; $R^2$ represents

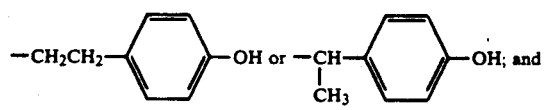

m and n are each 0 or a positive integer, provided that the sum of m and n is at least 1 and at least one $R^1$ is $R^2$, which comprises cleaving the t-butoxy ether groups of a corresponding siloxane product consisting essentially of at least one

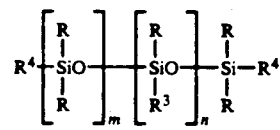

wherein R represents an alkyl group of 1 to 4 carbon atoms; $R^3$ represents a monovalent organic groups of 1 to 20 carbon atoms; m and n are each 0 or a positive integer and the sum of m and n is at least 1; and $R^4$ is R,

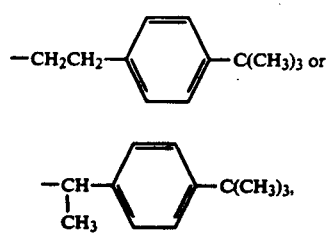

provided that at least one $R^4$ is not R.

2. The process of claim 1, wherein the ether cleavage is conducted at room temperature with concentrated hydrochloric acid and methanol at room tmeperature.

3. The process of claimn 1, wherein the starting t-butoxy ether group-containing product is produced by condensing a corresponding siloxane in which at least one of the $R^4$ groups is a hydrogen atom with p-tert-butoxystyrene.

4. The process of claim 1, wherein R and $R^3$ each is $CH_3$.

5. A process to prepare the hydroxyphenyl group-containing siloxane compound of claim 1 comprising stirring a mixture of an organic solvent, methanol, concnetrated hydrochloric acid and the following compound

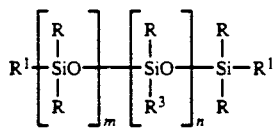

at room temperature, wherein R represents an alkyl group of 1 to 4 carbon atoms; $R^3$ represents a monovalent organic group of 1 to 20 carbon atoms; m and n are each 0 or a positive integer and $m+n\neq 0$.

6. The process of claim 1, wherein said organic solvent is at least one selected from ethers and aromatic hydrocarbons.

7. The process of claim 1, wherein the concentrated hydrochloric acid used in an amount of 0.5–3.0 g per 10 m moδ of the hydroxyphenyl group.

8. The process of claim 7, the amount of the concentrated hydrochloric acid is 1.0–2.0 g.

* * * * *